United States Patent [19]

Berg et al.

[11] Patent Number: 4,826,576

[45] Date of Patent: * May 2, 1989

[54] SEPARATION OF ISOPROPYL ACETATE FROM ISOPROPANOL BY EXTRACTIVE DISTILLATION

[75] Inventors: Lloyd Berg, 1314 So. Third Ave., Bozeman, Mont. 59715; An-I Yeh, Bozeman, Mont.

[73] Assignee: Lloyd Berg, Bozeman, Mont.

[*] Notice: The portion of the term of this patent subsequent to Apr. 5, 2000 has been disclaimed.

[21] Appl. No.: 869,733

[22] Filed: Jun. 2, 1986

Related U.S. Application Data

[63] Continuation-in-part of Ser. No. 768,331, Aug. 22, 1985, abandoned.

[51] Int. Cl.$^4$ .................. B01D 3/40; C07C 67/54
[52] U.S. Cl. ............................ 203/56; 203/57; 203/58; 203/59; 203/60; 203/63; 203/64; 560/248; 568/913
[58] Field of Search ............... 203/64, 56, 57, 60, 203/51, 59, 63, 58; 560/248, 234; 568/913, 918

[56] References Cited

U.S. PATENT DOCUMENTS

| | | | |
|---|---|---|---|
| 2,489,619 | 11/1949 | Carlson et al. | 203/98 |
| 2,559,519 | 7/1951 | Smith et al. | 203/84 |
| 2,559,520 | 7/1951 | Smith et al. | 203/64 |
| 2,575,285 | 11/1951 | Carlson et al. | 203/84 |
| 2,636,050 | 4/1953 | Hoaglin et al. | 560/248 |
| 4,379,028 | 4/1983 | Berg et al. | 203/51 |
| 4,431,838 | 2/1984 | Feldman et al. | 203/69 |
| 4,592,805 | 6/1986 | Berg et al. | 203/56 |
| 4,676,874 | 6/1987 | Berg et al. | 203/56 |
| 4,690,734 | 9/1987 | Berg et al. | 203/56 |
| 4,695,350 | 9/1987 | Berg et al. | 203/51 |

FOREIGN PATENT DOCUMENTS

| | | | |
|---|---|---|---|
| 1088040 | 9/1960 | Fed. Rep. of Germany | 203/64 |
| 1089744 | 9/1960 | Fed. Rep. of Germany | 203/64 |
| 119411 | 9/1979 | Japan | 203/64 |
| 815774 | 7/1959 | United Kingdom | 560/248 |

Primary Examiner—Wilbur Bascomb

[57] ABSTRACT

Isopropyl acetate cannot be completely removed from isopropyl acetate—isopropanol—water mixtures by distillation because of the presence of the minimum ternary azeotrope. Isopropyl acetate can be readily removed from mixtures containing it, isopropanol and water by using extractive distillation in which the extractive agent is a mixture of a polyol and one or higher boiling oxygenated, nitrogenous and/or sulfur containing organic compounds. Typical examples of effective agents are 1,3-butanediol and dimethylsulfoxide; 1,2,6-hexanetriol, dimethylsulfoxide and dimethylformamide.

2 Claims, No Drawings

SEPARATION OF ISOPROPYL ACETATE FROM ISOPROPANOL BY EXTRACTIVE DISTILLATION

This application is a continuation in part of U.S. patent application Ser. No. 06/768,331 filed Aug. 22, 1985 by Lloyd Berg and An-I Yeh which is also directed to the separation of isopropyl acetate from isopropanol by extractive distillation and now abandoned.

FIELD OF THE INVENTION

This invention relates to a method for separating isopropyl acetate from isopropanol using certain higher boiling liquids as the extractive agent in extractive distillation.

DESCRIPTION OF PRIOR ART

Extractive distillation is the method of separating close boiling compounds or azeotropes by carrying out the distillation in a multi-plate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plaltes to effect the same separation or make possible a greater degree of separation with the same number of plates. When the compounds to be separated normally form an azeotrope, the proper agents will cause them to boil separately during extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the most volatile component. This usually requires that the extractive agent boil twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

One of the commercially important ways to manufacture isopropyl acetate is by the catalytic esterification of isopropanol with acetic acid. Isopropyl acetate (b.p.=88.7° C.), isopropanol (b.p.=82.3° C.) and water (b.p.=100° C.) form a ternary azeotrope boiling at 75.5° C. containing 76 wt. % isopropyl acetate, 13 wt. % isopropanol and 11 wt. % water. Isopropyl acetate also forms a binary azeotrope with isopropanol which boils at 80.1° C. and contains 47.4 wt. % isopropyl acetate and a binary azeotrope with water boiling at 75.9° C. containing 88.9 wt. % isopropyl acetate. Isopropanol also forms a binary minimum azeotrope with water which boils at 80.4° C. and contains 87.8 wt. % isopropanol. Thus in the esterification of isopropanol with acetic acid to form isopropyl acetate and water, the rectification of this mixture has three binary and one ternary azeotrope to content with, and yields the lowest boilign constituent, namely the isopropyl acetate—isopropanol—water ternary azeotrope. It is therefore impossible to produce isopropyl acetate from isopropanol and water mixtures by rectification because the lower boiling ternary azeotrope will always come off overhead as the initial product. Any mixture of isopropyl acetate, isopropanol and water subjected to rectification at one atmosphere pressure will produce an overhead product boiling at 75.5° C. and containing 76 wt. % isopropyl acetate, 13 wt. % isopropanol and 11 wt. % water. Extractive distillation would be an attractive method of effecting the separation of isopropyl acetate from isopropanol if agents can be found that (1) will break the isopropyl acetate—isopropanol—water azeotrope and (2) are easy to recover from the isopropanol, that is, form no azeotrope with isopropanol and boil sufficiently above isopropanol to make the separation by rectification possible with only a few theoretical plates.

Extractive distillation typically requires the addition of an equal amount to twice as much extractive agent as the isopropyl acetate—isopropanol—water on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is to be done by azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is also desirable that the extractive agent be miscible with isopropanol otherwise it will form a two-phase azeotrope with isopropanol in the recovery column and some other method of separation will have to be employed. Japanese Patent No. 55-4119-411 describes the separation of methyl acetate from methanol using ethylene glycol as the extractive distillation agent. Berg & Ratanapupech, U.S. Pat. Nos. 4,379,028 and 4,569,726 described the separation of ethyl acetate from ethanol. Berg & Yeh, U.S. Pat. No. 4,592,805 described the separation of n-propyl acetate from n-propanol and Berg & Yeh, U.S. Pat. Nos. 4,507,176 and 4,525,245 described the separation of n-butyl acetate from n-butanol. British Pat. No. 815,774, July 1, 1959 describes a process to separate esters from alcohols using polyhydric alcohols as the extractive distillation agent.

We investigated the efficiency of the pure individual polyols (also called glycols or polyhydric alcohols) and obtained the results shown in Table 1. Their performance ranged from a relative volatility of 2.2 for ethylene glycol to 1.2 for hexylene glycol in the separation of isopropyl acetate from isopropanol. The material investigated was the azeotrope which possesses a relative volatility of 1.0.

TABLE 1

The Relative Volatility of Several Pure Polyols as the Agent for Isopropyl Acetate from Isopropanol

| Polyol | Relative Volatility |
| --- | --- |
| Ethylene glycol | 2.2 |
| Propylene glycol | 1.6 |
| 1,3-Butanediol | 1.7 |

TABLE 1-continued

The Relative Volatility of Several Pure Polyols as the Agent for Isopropyl Acetate from Isopropanol

| Polyol | Relative Volatility |
|---|---|
| 1,4-Butanediol | 1.7 |
| 1,5-Pentanediol | 1.5 |
| 1,6-Hexanediol | 1.6 |
| Hexylene glycol | 1.2 |
| Glycerine | 0 (2-phase) |
| 1,2,6-Hexanetriol | 0 (2-phase) |
| Diethylene glycol | 1.9 |
| Triethylene glycol | 1.7 |
| Tetraethylene glycol | 1.5 |
| Polyethylene glycol | 1.3 |
| Dipropylene glycol | 1.3 |
| Polypropylene glycol | 1.3 |

The effect of relative volatility on column performance can be deduced by referring to Table 2. Here we have listed the theoretical plates required to separate the isopropyl acetate from isopropanol in either 95% purity or 98% purity. The data in Table 2 is based on total reflux, theoretical plates and actual plates. Actual plates are about 75% efficient and actual reflux ratios employed further increase the actual plate requirement. Table 2 shows that if ethylene glycol, relative volatility=2.2 is employed, it will require at least 49 actual plates to produce products in 98% purity and at least 20 actual plates to produce products in 95% purity. If extractive distillation agents could be found that will increase the relative volatility to 3, Table 2 shows that only 19 actual plates are required for 98% purity or ten actual plates for 95% purity.

TABLE 2

Number of Plates Required For 98% and 95% Purity Separation

| Relative Volatility | 98% Purity Theor. Plates | Actual Plates | 95% Purity Theor. Plates | Actual Plates |
|---|---|---|---|---|
| 1.3 | 450 | 600 | 91 | 121 |
| 1.5 | 200 | 267 | 50 | 67 |
| 1.7 | 105 | 140 | 32 | 43 |
| 2.0 | 51 | 73 | 19 | 26 |
| 2.2 | 37 | 49 | 15 | 20 |
| 2.5 | 24 | 32 | 11 | 15 |
| 2.7 | 19 | 26 | 9 | 12 |
| 3.0 | 14 | 19 | 7 | 10 |
| 3.5 | 10 | 14 | 6 | 8 |

OBJECTIVE OF THE INVENTION

The object of this invention is to provide a process or method of extractive distillation that will enhance the relative volatility of isopropyl acetate from isopropanol in their separation in a rectification column. It is a further object of this invention to identify suitable extractive distillation agents which will eliminate the isopropyl acetate—isopropanol—water ternary azeotrope and make possible the production of pure isopropyl acetate and isopropanol by rectification. It is a further object of this invention to identify organic compounds which, in addition to the above constraints, are stable, can be separated from isopropanol by rectification with relatively few theoretical plates and can be recycled to the extractive distillation column and reused with little decomposition.

SUMMARY OF THE INVENTION

The objects of the invention are provided by a process for separating isopropyl acetate from isopropanol which entails the use of certain oxygenated, nitrogenous and/or sulfur containing organic compounds as the agent in extractive distillation.

TABLE 3

Some Polyol Containing Mixtures Which Are Effective Extractive Distillation Agents In Separating Isopropyl Acetate From Isopropanol

| Compounds | Ratios | | Relative Volatilities | |
|---|---|---|---|---|
| Ethylene glycol, N—Methyl ethanolamine | $(1/2)^2$ | $(3/5)^2$ | 2.70 | — |
| Ethylene glycol, Methyl diethanolamine | " | " | 2.05 | 2.51 |
| Ethylene glycol, Isopropanolamine | " | " | 2.41 | 2.79 |
| Ethylene glycol, Ethanolamine | " | " | 3.39 | |
| Ethylene glycol, N—Methyl pyrrolidone | " | " | 2.16 | 2.40 |
| Ethylene glycol, DMSO, Ethanolamine | $(1/3)_3$ | $(2/5)^3$ | 2.89 | 2.84 |
| Ethylene glycol, DMSO, Triethanolamine | " | " | 2.21 | 2.27 |
| Ethylene glycol, DMSO, Acetamide | " | " | 2.26 | 2.45 |
| Ethylene glycol, DMSO, N—Methyl ethanolamine | " | | 2.16 | |
| Ethylene glycol, DMSO, Methyl diethanolamine | " | " | 2.51 | 1.81 |
| Ethylene glycol, DMSO, Isopropanolamine | " | " | 2.15 | 2.38 |
| Ethylene glycol, DMSO, N—Methylpyrrolidone | " | | 2.81 | |
| Ethylene glycol, DMFA, Ethanolamine | " | | 2.28 | |
| Ethylene glycol, DMFA, N—Methyl ethanolamine | " | " | 2.08 | 2.28 |
| Propylene glycol, Ethanolamine | $(1/2)^2$ | $(3/5)^2$ | 2.49 | |
| 1,3-Butanediol, Ethanolamine | " | " | 2.50 | |
| 1,3-Butanediol, DMSO | " | " | 2.12 | 2.67 |
| 1,3-Butanediol, DMSO, Ethanolamine | $(1/3)^3$ | $(2/5)^3$ | 2.23 | |
| 1,4-Butanediol, Ethanolamine | $(1/2)^2$ | $(3/5)^2$ | 2.88 | |
| 1,4-Butanediol, N—Methyl ethanolamine | " | " | 2.17 | |
| 1,4-Butanediol, Triethanolamine | " | " | 2.11 | 2.53 |
| 1,4-Butanediol, DMSO, Ethanolamine | $(1/3)^3$ | $(2/5)^3$ | 2.63 | |
| 1,4-Butanediol, DMSO, Triethanolamine | " | " | 2.43 | 2.43 |
| 1,5-Pentanediol, Ethanolamine | $(1/2)^2$ | $(3/5)^2$ | 2.41 | |
| 1,5-Pentanediol, DMSO, Acetamide | $(1/3)^3$ | $(2/5)^3$ | 2.08 | 2.00 |
| 1,5-Pentanediol, DMSO, Ethanolamine | " | " | 2.17 | |
| 1,6-Hexanediol, Ethanolamine | $(1/2)^2$ | $(3/5)^2$ | 2.83 | |
| 1,6-Hexanediol, Triethanolamine | " | " | 2.14 | 2.46 |
| 1,6-Hexanediol, DMSO, Ethanolamine | $(1/3)^3$ | $(2/5)^3$ | 2.05 | |
| 1,6-Hexanediol, DMSO, Triethanolamine | " | " | 2.32 | 1.93 |
| Hexylene glycol, Ethanolamine | $(1/2)^2$ | $(3/5)^2$ | 2.12 | |

TABLE 3-continued

Some Polyol Containing Mixtures Which Are Effective
Extractive Distillation Agents In Separating Isopropyl Acetate From Isopropanol

| Compounds | Ratios | | Relative Volatilities | |
|---|---|---|---|---|
| Glycerine, DMSO | " | " | 2.60 | 2.62 |
| Glycerine, DMSO, N—Methyl pyrrolidone | $(1/3)^3$ | $(2/5)^3$ | 2.04 | 2.24 |
| Glycerine, DMSO, Ethanolamine | " | " | 2.47 | |
| Glycerine, DMSO, N—Methyl ethanolamine | " | " | 2.33 | |
| Glycerine, DMSO, DMFA | " | " | 1.99 | 2.29 |
| Glycerine, DMFA, Ethanolamine | " | " | 3.22 | |
| Glycerine, DMFA, N—Methyl ethanolamine | " | " | 2.79 | |
| 1,2,6-Hexanetriol, DMSO | $(1/2)^2$ | $(3/5)^2$ | 2.06 | 2.14 |
| 1,2,6-Hexanetriol, DMSO, DMFA | $(1/3)^3$ | $(2/5)^3$ | 2.17 | 2.13 |
| 1,2,6-Hexanetriol, DMFA, Ethanolamine | " | " | 2.89 | |
| 1,2,6-Hexanetriol, DMFA, DMSO, Ethanolamine | $(1/4)^4$ | | 2.66 | |
| Diethylene glycol | $(1/2)^2$ | $(3/5)^2$ | 2.67 | |
| Diethylene glycol, DMSO | " | " | 2.21 | 2.18 |
| Diethylene glycol, DMSO, Ethanolamine | $(1/3)^3$ | $(2/5)^3$ | 2.30 | |
| Diethylene glycol, DMSO, Acetamide | " | " | 2.13 | 2.00 |
| Triethylene glycol, Ethanolamine | $(1/2)^2$ | $(3/5)^2$ | 2.60 | |
| Triethylene glycol, DMSO | " | " | 2.20 | 2.09 |
| Triethylene glycol, DMSO, Acetamide | $(1/3)^3$ | $(2/5)^3$ | 2.00 | 2.08 |
| Triethylene glycol, DMSO, Ethanolamine | " | " | 2.35 | |
| Tetraethylene glycol, Ethanolamine | $(1/2)^2$ | $(3/5)^2$ | 2.42 | |
| Tetraethylene glycol, DMSO, Ethanolamine | $(1/3)^3$ | $(2/5)^3$ | 2.46 | |
| Tetraethylene glycol, DMFA, Acetamide | " | " | 2.05 | 2.15 |
| Polyethylene glycol, Ethanolamine | $(1/2)^2$ | $(3/5)^2$ | 2.98 | |
| Polyethylene glycol, DMSO, Acetamide | $(1/3)^3$ | $(2/5)^3$ | 2.08 | 2.06 |
| Polyethylene glycol, DMSO, Ethanolamine | " | " | 2.07 | |
| Dipropylene glycol, Ethanolamine | $(1/2)^2$ | $(3/5)^2$ | 2.09 | |
| Dipropylene glycol, DMSO, Ethanolamine | $(1/3)^3$ | | 2.09 | |

DETAILED DESCRIPTION OF THE INVENTION

We have discovered that polyols when mixed with certain oxygenated, nitrogenous and/or sulfur containing organic compounds will effectively negate the isopropyl acetate—isopropanol—water ternary azeotrope and permit the separation of isopropyl acetate from isopropanol by rectification when employed as the agent in extractive distillation. Table 3 lists a number of polyols with their mixtures and approximate proportions that we have found to be effective. The data in Table 3 was obtained in a vapor-liquid equilibrium still. In each case, the starting material was the isopropyl acetate—isopropanol—water azeotrope. The ratios are the parts by weight of extractive agent used per part of the isopropyl acetate—isopropanol—water azeotrope. The relative volatilities are listed for each of the two ratios employed. The polyols that are effective are ethylene glycol, propylene glycol, 1,3-butanediol, 1,4-butanediol, 1,5-pentanediol, 1,6-hexanediol, hexylene glycol, glycerine, 1,2,6-hexanetriol, diethylene glycol, triethylene glycol, tetraethylene glycol, polyethylene glycol and dipropylene glycol. The compounds, in addition to the above, which are effective when used with polyols in mixtures of two or more components are dimethylsulfoxide, dimethylformamide, acetamide, ethanolamine, triethanolamine, N-methyl ethanolamine, methyl diethanolamine, isopropanolamine and N-methyl pyrrolidone.

The two relative volatilities shown in Table 3 correspond to the two different ratios employed. For example, in Table 3, one half part of ethylene glycol mixed with one half part of isopropanolamine with one part of the isopropyl acetate—isopropanol—water azeotrope gives a relative volatility of 2.41, 3/5 parts of ethylene glycol plus 3/5 parts of isopropanolamine gives 2.79. One third parts of ethylene glycol plus ⅓ parts of dimethylsulfoxide(DMSO) plus ⅓ parts of acetamide mixed with one part of the isopropyl acetate—isopropanol—water azeotrope gives a relative volatility of 2.26, with 2/5 parts, these three give 2.45. In every example in Table 3, the starting material is the isopropyl acetate—isopropanol—water azeotrope which possesses a relative volatility of 1.0.

Several of the compounds and mixtures listed in Table 3 whose relative volatility had been determined in the vapor-liquid equilibrium still, were then evaluated in a glass perforated plate rectification column possessing 4.5 theoretical plates. The isopropyl acetate—isopropanol—water mixture studied contained 76 wt. % isopropyl acetate, 13 wt. % isopropanol and 11 wt. % water which is the azeotrope composition. In every case, the overhead was richer than 76 wt. % isopropyl acetate and the results are tabulated in Table 4. Without the extractive agent, the overhead would be the azeotrope, 76 wt. % isopropyl acetate. This proves that the extractive agent is negating the azeotrope and makes rectification proceed as if the azeotrope no longer exists and brings the more volatile components, isopropyl acetate and water, out as overhead.

TABLE 4

Data From Runs Made In Rectification Column

| Agent | Wt. % Isopropyl Acetate | | Relative Volatility |
|---|---|---|---|
| | Overhead | Bottoms | |
| Blank | 84.6 | 82.6 | 1.03 |
| Ethylene glycol + Isopropanolamine | 99.0 | 61.5 | 2.5 |
| Ethylene glycol + Ethanolamine | 99.7 | 57.1 | 3.4 |

Initial Mixture: 304 g. Isopropyl acetate + 52 g. Isopropanol + 44 g. Water
Blank: No agent used.
Agents added at 20 ml/min. and 65° C.

The data in Table 4 was obtained in the following manner. The charge was 76 wt. % isopropyl acetate, 13 wt. % isopropanol and 11 wt. % water and after a half hour of operation in the 4.5 theoretical plate column to establish equilibrium, a 50—50 mixture of ethylene glycol and isopropanolamine at 65° C. and 20 ml/min. was pumped in. The rectification was contained for 1.5 hours with sampling of the overhead and bottoms after one hour and 1.5 hours. The average of the two analyses was 99.0 wt. % isopropyl acetate in the overhead and 61.5 wt. % in the bottoms, both on a water-free basis which gives a relative volatility of 2.51 of isopropyl acetate to isopropanol. This indicates that the ternary azeotrope has been negated and separation accomplished. The isopropyl acetate comes off in the form of its binary azeotrope with water which on condensation, immediately forms two liquid layers. The solubility of isopropyl acetate in water is only 3%.

THE USEFULNESS OF THE INVENTION

The usefulness or utility of this invention can be demonstrated by referring to the data presented in Tables 3 and 4. All of the successful extractive distillation agents show that isopropyl acetate, isopropanol and water can be separated from their ternary azeotrope by means of distillation in a rectification column and that the ease of separation as measured by relative volatility is considerable. Without these extractive distillation agents, no improvement above the azeotrope composition will occur in a rectification column. The data also show that the most attractive agents will operate at a boilup rate low enough to make this a useful and efficient method of recovering high purity isopropyl acetate from any mixture of these three including the ternary minimum azeotrope. The stability of the compounds used and the boiling point difference is such that complete recovery is obtainable by a simple distillation and the amount required for make-up is small.

WORKING EXAMPLES

Example 1

The isopropyl acetate—isopropanol—water azeotrope is 76 wt. % isopropyl acetate, 13 wt. % isopropanol and 11 wt. % water. Fifty grams of the isopropyl acetate—isopropanol—water azeotrope, 25 grams of 1,3-butanediol and 25 grams of dimethylsulfoxide (DMSO) were charged to the water vapor-liquid equilibrium still and refluxed for 12 hours. Analyses indicated a vapor composition of 94.7% isopropyl acetate, 5.3% isopropanol; a liquid composition of 89.5% isopropyl acetate, 10.5% isopropanol which is a relative volatility of 2.12. Five grams of 1,3-butanediol and five grams of DMSO were added and refluxing continued for another eleven hours. Analyses indicated a vapor composition of 95.1% isopropyl acetate, 4.9% isopropanol; a liquid composition of 87.9% isopropyl acetate, 12.1% isopropanol which is a relative volatility of 2.67.

Example 2

Fifty grams of the isopropyl acetate—isopropanol—water azeotrope, 17 grams of 1,2,6-hexanetriol, 17 grams of DMSO and 17 grams of dimethylformamide (DMFA) were charged to the vapor-liquid equilibrium still and refluxed for 18 hours. Analyses indicated a vapor composition of 84.5% isopropyl acetate, 15.1% isopropanol; a liquid composition of 72.1% isopropyl acetate, 27.9% isopropanol which is a relative volatility of 2.17. Three grams each of 1,2,6-hexanetriol, DMSO and DMFA were added and refluxing continued for another nine hours. Analyses indicated a vapor composition of 84.7% isopropyl acetate, 15.3% isopropanol; a liquid composition of 72.2% isopropyl acetate, 27.8% isopropanol which is a relative volatility of 2.13.

Example 3

A glass perforated plate rectification column was calibrated with ethylbenzene and p-xylene which possesses a relative volatility of 1.06 and found to have 4.5 theoretical plates. A solution of 304 grams of isopropyl acetate, 52 grams of isopropanol and 44 grams of water was placed in the stillpot and heated. When refluxing began, an extractive agent comprising 50% ethylene glycol and 50% isopropanolamine was pumped into the column at a rate of 20 ml/min. The temperature of the extractive agent as it entered the column was 65° C. After establishing the feed rate of the extractive agent, the heat input to the isopropyl acetate, isopropanol and water in the stillpot was adjusted to give a total reflux of 10–20 ml/min. After one hour of operation, the overhead and bottoms samples of approximately two ml. were collected and analysed using gas chromatography. The overhead analyses were 99% isopropyl acetate, 1% isopropanol. The bottoms anlayses were 61.5% isopropyl acetate, 38.5% isopropanol. Using these compositions in the Fenske equation, with the number of theoretical plates in the column being 4.5, gave an average relative volatility of 2.5 for each theoretical plate. After 1½ hours of total operating time, the overhead and bottoms samples were again taken and analysed. The overhead composition was 99.1% isopropyl acetate, 0.9% isopropanol and the bottoms composition was 62.5% isopropyl acetate, 37.5% isopropanol. This gave an average relative volatility of 2.52 for each theoretical plate.

What is claimed is:

1. A method for recovering isopropyl acetate from a mixture of isopropyl acetate, isopropanol and water which comprises distilling a mixture of isopropyl acetate, isopropanol and water in a rectification column in the presence of about one part of extractive agent per part of isopropyl acetate—isopropanol—water mixture, recovering isopropyl acetate and water in the form of a binary azeotrope as overhead product, condensing said overhead product to obtain two separate liquid layers of said condensed overhead product and obtaining the extractive agent and isopropanol from the stillpot, the extractive agent comprises a mixture of propylene glycol and ethanolamine.

2. A method for recovering isopropyl acetate from a mixture of isopropyl acetate, isopropanol and water which comprises distilling a mixture of isopropyl acetate, isopropanol and water in rectification column in the presence of about one part of extractive agent per part of isopropyl acetate—isopropanol—water mixture, recovering isopropyl acetate and water in the form of a binary azeotrope as overhead product, condensing said overhead product to obtain two separate liquid layers of said condensed overhead product and obtaining the extractive agent and isopropanol from the stillpot, the extractive agent comprises a mixture of hexylene glycol and ethanolamine.

* * * * *